(12) United States Patent
Jin

(10) Patent No.: US 10,578,841 B2
(45) Date of Patent: Mar. 3, 2020

(54) INFRARED OPTICAL SYSTEM, IMAGING OPTICAL DEVICE, AND DIGITAL APPLIANCE

(71) Applicant: KONICA MINOLTA, INC., Chiyoda-ku, Tokyo (JP)

(72) Inventor: Makoto Jin, Sakai (JP)

(73) Assignee: KONICA MINOLTA, INC., Tokyo (JP)

( * ) Notice: Subject to any disclaimer, the term of this patent is extended or adjusted under 35 U.S.C. 154(b) by 325 days.

(21) Appl. No.: 15/577,056

(22) PCT Filed: May 20, 2016

(86) PCT No.: PCT/JP2016/065011
§ 371 (c)(1),
(2) Date: Nov. 27, 2017

(87) PCT Pub. No.: WO2016/190243
PCT Pub. Date: Dec. 1, 2016

(65) Prior Publication Data
US 2018/0157012 A1 Jun. 7, 2018

(30) Foreign Application Priority Data
May 27, 2015 (JP) ................................ 2015-107124

(51) Int. Cl.
*G02B 13/14* (2006.01)
*G02B 13/18* (2006.01)
(Continued)

(52) U.S. Cl.
CPC ............ *G02B 13/14* (2013.01); *G01J 5/0014* (2013.01); *G01J 5/061* (2013.01); *G02B 5/006* (2013.01);
(Continued)

(58) Field of Classification Search
CPC ........ G02B 13/14; G02B 13/18; G02B 13/03; G02B 5/208; H04N 5/33; H04N 5/2254
See application file for complete search history.

(56) References Cited

U.S. PATENT DOCUMENTS

2012/0229892 A1 9/2012 Kang et al.

FOREIGN PATENT DOCUMENTS

JP 2003185919 A 7/2003

OTHER PUBLICATIONS

International Search Report for corresponding Application No. PCT/JP2016/065011; dated Jul. 19, 2016.

*Primary Examiner* — William R Alexander
*Assistant Examiner* — Tamara Y. Washington
(74) *Attorney, Agent, or Firm* — Cantor Colburn LLP

(57) ABSTRACT

This infrared optical system using the wavelength range of 3 to 5 μm comprises, in the order from an object side, a first lens having a negative power and formed with a convex meniscus toward an object, a second lens that is convex on both sides, and a cold aperture. A bandpass filter is provided between the second lens and the image surface. The first and second lenses are configured with silicon or germanium with each provided with an aspheric surface at least on one side. The infrared optical system satisfies the conditional expressions: 0.1 μm<λ2−λ1<1 μm, 3 μm<λ1<5 μm, and 3 μm<λ2<5 μm. (Where λ1 and λ2 respectively represent a wavelength near the shorter wavelengths and a wavelength near the longer wavelengths in a half width of the transmission wavelength region of the bandpass filter).

9 Claims, 8 Drawing Sheets

(51) Int. Cl.
*G02B 5/00* (2006.01)
*G01J 5/00* (2006.01)
*G01J 5/06* (2006.01)
*G02B 5/20* (2006.01)
*G01N 21/3504* (2014.01)
*G02B 9/10* (2006.01)
*H04N 5/232* (2006.01)
*H04N 5/33* (2006.01)

(52) U.S. Cl.
CPC ............. *G02B 5/208* (2013.01); *G02B 13/18* (2013.01); *G01J 2005/0077* (2013.01); *G01N 21/3504* (2013.01); *G02B 9/10* (2013.01); *H04N 5/23245* (2013.01); *H04N 5/33* (2013.01)

FIG.1
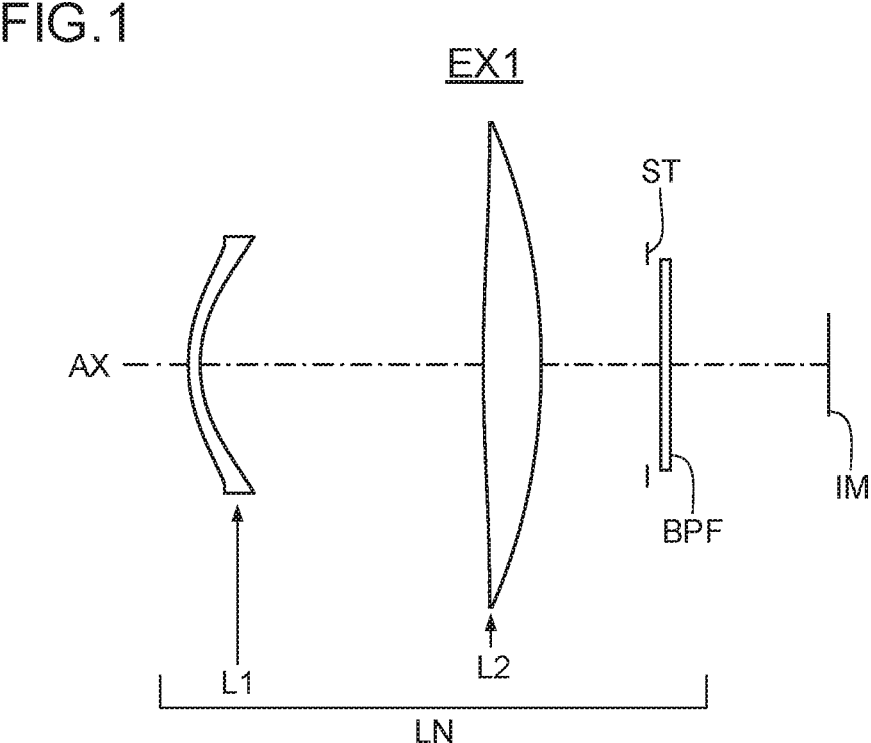
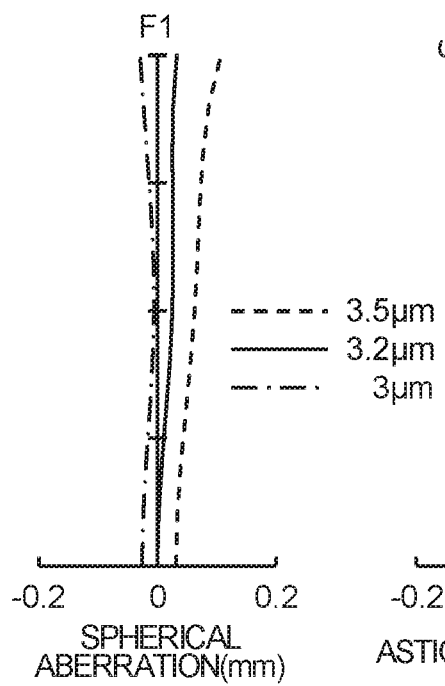
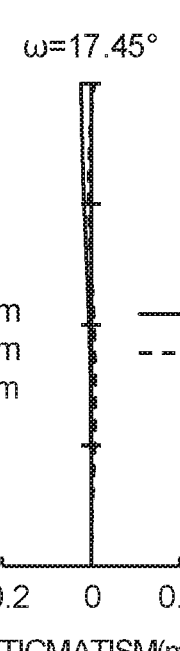
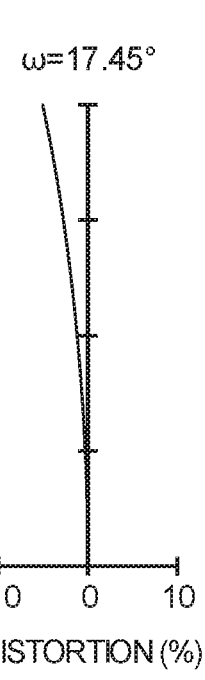

EX2

EX2

EX2

FIG.5
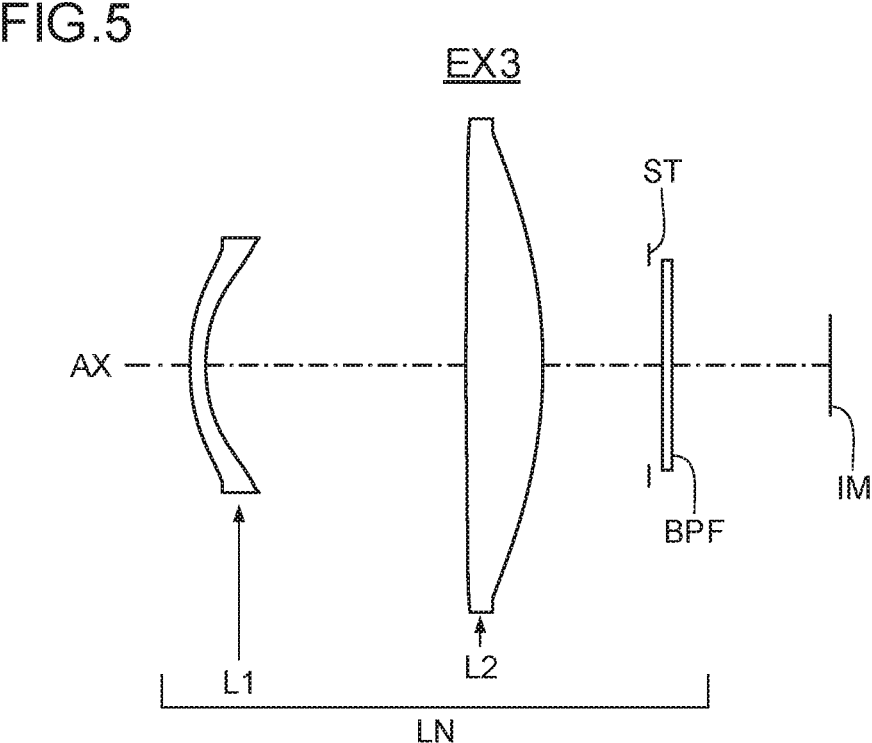
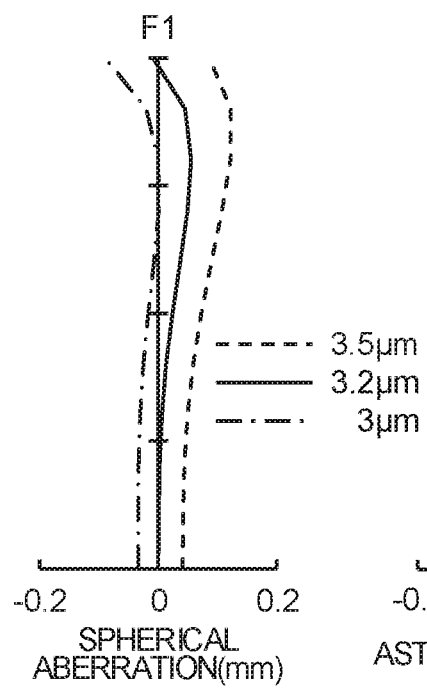
FIG.6A
EX3
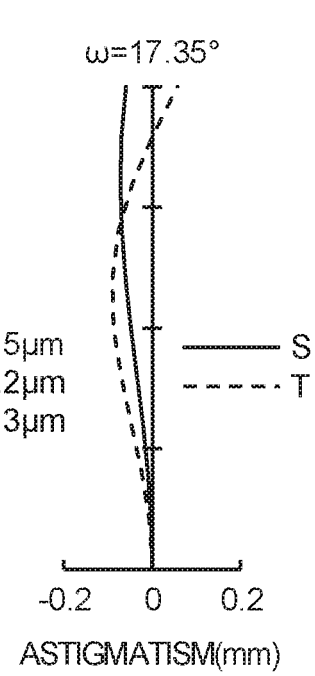
FIG.6B
EX3
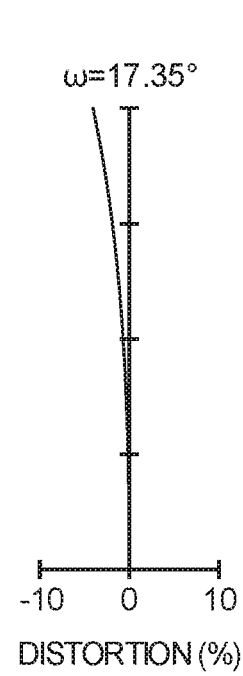
FIG.6C
EX3

EX4

EX4

EX4

FIG.9
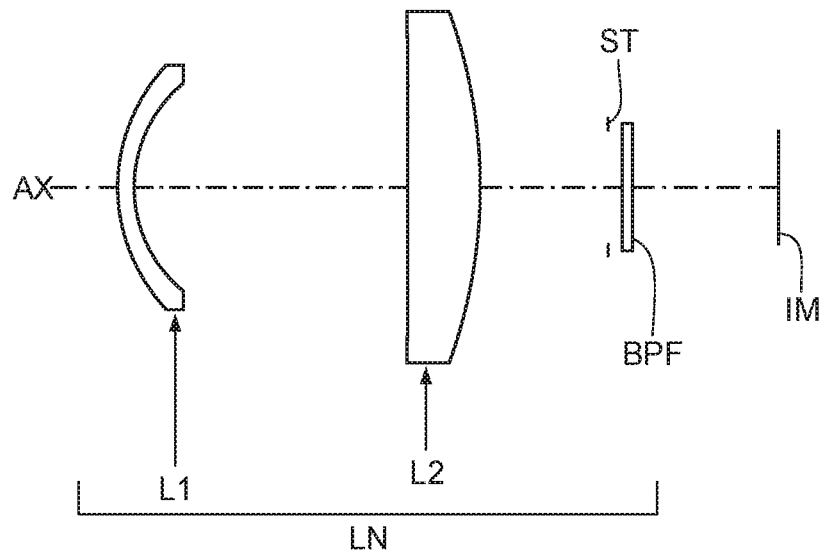
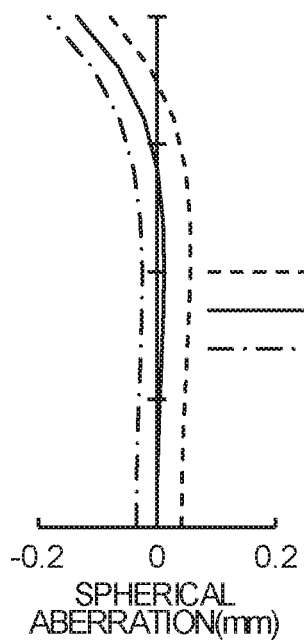
FIG.10A
EX5
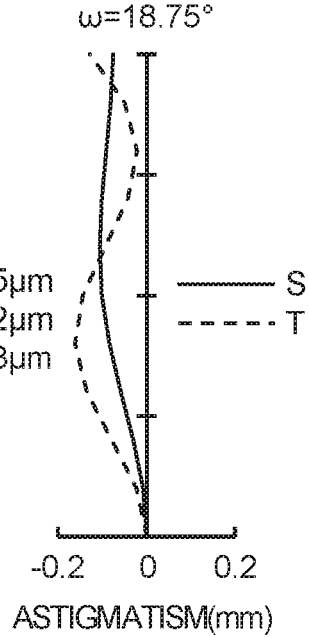
FIG.10B
EX5
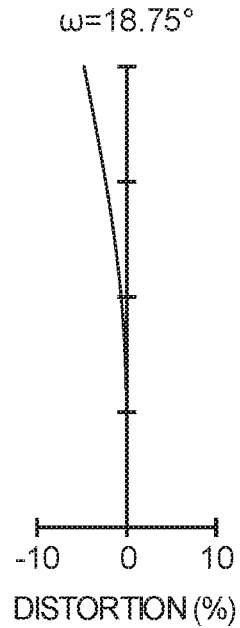
FIG.10C
EX5

EX6

EX6

EX6

EX6

FIG.13   EX7
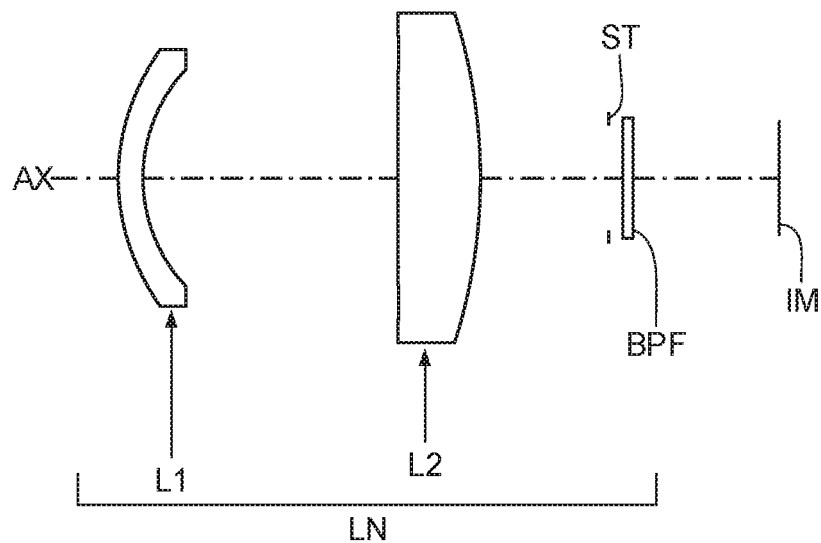
FIG.14A  
EX7
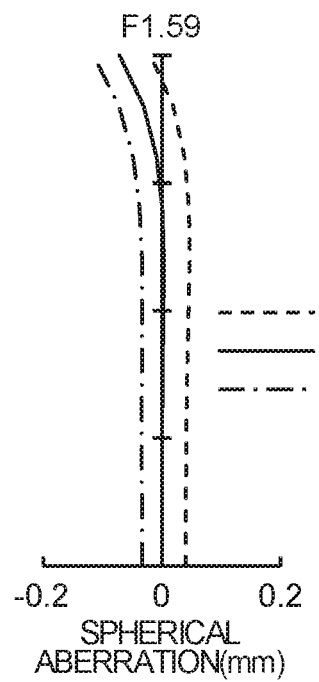
FIG.14B  
EX7
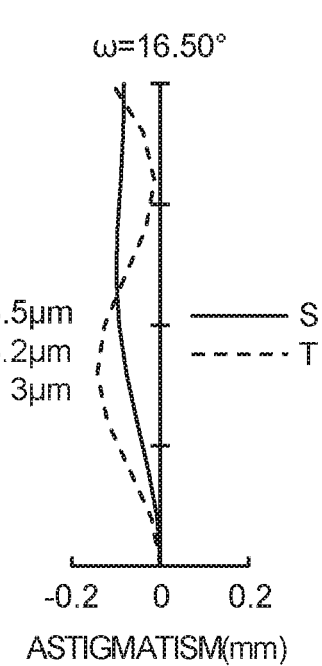
FIG.14C  
EX7
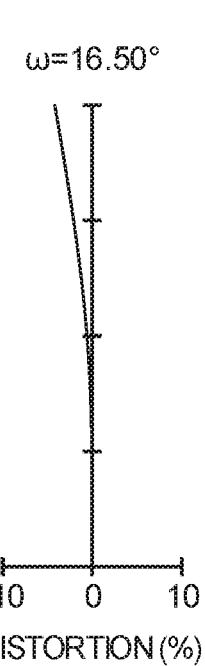

INFRARED OPTICAL SYSTEM, IMAGING OPTICAL DEVICE, AND DIGITAL APPLIANCE

CROSS REFERENCE TO RELATED APPLICATIONS

The present U.S. patent application is a U. S. National Phase Application under 35 USC 371 of International Application PCT/JP2016/065011, filed on May 20, 2016. Priority under 35 U.S.C § 119(a) and 35 U.S.C. § 365(b) is claimed from Japanese Application No. 2015-107124, filed on May 27, 2015, the entirety of which is incorporated herein by references.

TECHNICAL FIELD

The present invention relates to an infrared optical system, an imaging optical device, and a digital appliance. More particularly, the present invention relates to an infrared optical system for gas detection for use as an imaging optical system in an infrared region spanning over the wavelength band of 3 to 5 μm, an imaging optical device in which an infrared image obtained through an infrared optical system is captured with an image sensor such as a cooled sensor, and a digital appliance furnished with an image input function that incorporates an infrared optical system.

BACKGROUND ART

It is known that the absorption wavelength bands peculiar to hydrocarbon-based substances such as methane, ethane, propane, and butane concentrate around the wavelength band of 3 to 5 μm. These hydrocarbon-based substances are gaseous at ordinary temperature and are flammable, and thus they require careful handling. For this reason, in recent years, it has been becoming increasingly common to image, with an infrared camera, contrast differences resulting from such absorption to detect a gas leak or the like that cannot be detected on the basis of visible light. The wavelength band of 3 to 5 μm is one in which the amount of light from the sun is small and the amount of light radiated from objects is small; thus, it is customary to cool sensors so that, even with a small amount of light, imaging can be performed with high sensitivity. Hence the demand for infrared optical systems that can be incorporated in cooled sensors and that provide high transmittance combined with satisfactory optical performance.

Examples of infrared optical systems are seen in Patent Documents 1 and 2 identified below. Patent Document 1 proposes an infrared optical system composed of three lens elements. Patent Document 2 proposes an infrared optical system composed of two lens elements. The infrared optical system disclosed in Patent Document 1 is composed of three germanium lens elements, namely a positive meniscus lens element convex to the object side, a negative lens element, and a positive meniscus lens element convex to the object side, and provides satisfactory optical performance in the wavelength band of 7 to 13 μm. The infrared optical system disclosed in Patent Document 2 is composed of two lens elements, namely a meniscus lens element convex to the image side and a biconvex lens element, both being germanium lens elements and each having an aspherical surface as one surface.

LIST OF CITATIONS

Patent Literature

Patent Document 1: Japanese Patent Application published as No. 2003-185919

Patent Document 2: US Patent Application published as No. 2012/0229892 A1

SUMMARY OF THE INVENTION

Technical Problem

In the infrared optical system disclosed in Patent Document 1, arranging a positive lens element as the first, a negative lens element as the second, and a positive lens element as the third helps achieve correction of various aberrations including chromatic aberration. However, this requires three lens elements, and leads to a loss of light on the lens surfaces.

In the infrared optical system disclosed in Patent Document 2, arranging an aperture stop between the first and second lens elements helps secure satisfactory optical performance with as few as two lens elements. Thus, in a case where it is used in a cooled sensor, apart from the aperture stop, a cold aperture needs to be arranged separately on the image surface side of the second lens element to shield all unnecessary light. In that case, however, the pupil cannot be aligned exactly, and this inconveniently leads to difficulty shielding all the light radiated from mechanical components such as a lens holding member.

Against the background discussed above, the present invention aims to provide an infrared optical system that can be incorporated in a cooled sensor and that achieves high transmittance and high optical performance with as few as two lens elements, and to provide an imaging optical device and a digital appliance provided with such an infrared optical system.

Means for Solving the Problem

To achieve at least one of the above-mentioned objects, according to an aspect of the present invention, an infrared optical system reflecting one aspect of the present invention, which is an infrared optical system for use for imaging in a wavelength band of 3 to 5 μm, comprises from the object side: a first lens element which has a negative optical power and which has a meniscus shape convex to the object side; a second lens element which has a biconvex shape; and a cold aperture, with a band-pass filter arranged between the second lens element and the image surface. The first lens element is formed of silicon or germanium, and has an aspherical surface as at least one surface thereof. The second lens element is formed of silicon or germanium, and has an aspherical surface as at least one surface thereof. Moreover, conditional formulae (1) to (3) below are fulfilled:

$$0.1 \text{ μm} < \lambda_2 - \lambda_1 < 1 \text{ μm} \tag{1}$$

$$3 \text{ μm} < \lambda_1 < 5 \text{ μm} \tag{2}$$

$$3 \text{ μm} < \lambda_2 < 5 \text{ μm} \tag{3}$$

where $\lambda_1$ represents the shorter wavelength-side wavelength of the half-maximum width of the transmission wavelength range of the band-pass filter; and $\lambda_2$ represents the longer wavelength-side wavelength of the half-maximum width of the transmission wavelength range of the band-pass filter.

Advantageous Effects of the Invention

According to the present invention, it is possible to provide an infrared optical system and an imaging optical device that can be incorporated in a cooled sensor and that achieves high transmittance and high optical performance with as few as two lens elements. By employing an infrared optical system or an imaging optical device according to the present invention in digital appliances such as gas detection devices and camera systems (for example, surveillance cameras, security cameras, vehicle-mounted cameras, and aircraft cameras), it is possible to add a high-performance infrared image input function to those digital appliances at low cost.

BRIEF DESCRIPTION OF DRAWINGS

The advantages and features provided by one or more embodiments of the invention will become more fully understood from the detailed description given herein below and the appended drawings which are given by way of illustration only, and thus are not intended as a definition of the limits of the present invention:

FIG. 1 is a lens arrangement diagram of a first embodiment (Example 1) of the present invention;

FIG. 2A to 2C are aberration diagrams of Example 1;

FIG. 5 is a lens arrangement diagram of a third embodiment (Example 3) of the present invention;

FIG. 6A to 6C are aberration diagrams of Example 3;

FIG. 9 is a lens arrangement diagram of a fifth embodiment (Example 5) of the present invention;

FIG. 10A to 10C are aberration diagrams of Example 5;

FIG. 13 is a lens arrangement diagram of a seventh embodiment (Example 7) of the present invention;

FIG. 14A to 14C are aberration diagrams of Example 7; and

DESCRIPTION OF EMBODIMENTS

Figure 3:
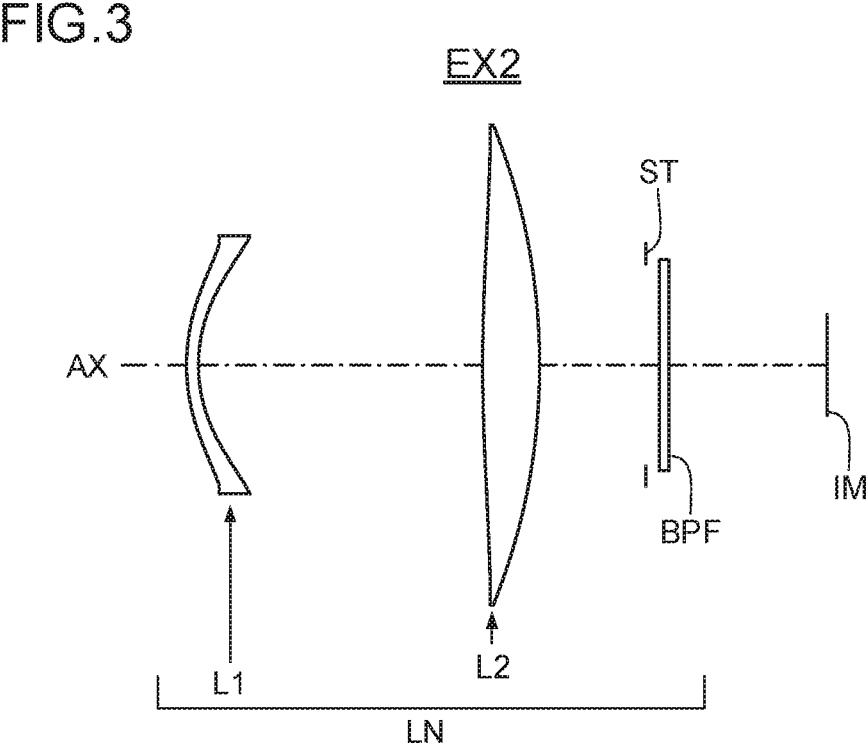
FIG. 3 is a lens arrangement diagram of a second embodiment (Example 2) of the present invention.

Hereinafter, one or more embodiments of the present invention will be described with reference to the drawings. However, the scope of the invention is not limited to the disclosed embodiments. An infrared optical system according to one embodiment of the present invention is an infrared optical system for use for imaging in a wavelength band of 3 to 5 μm, and is composed of, from the object side, a first lens element which has a negative optical power (an optical power being a quantity defined as the reciprocal of a focal length) and which has a meniscus shape convex to the object side, a second lens element which has a biconvex shape, and a cold aperture, with a band-pass filter arranged between the second lens element and the image surface. The first lens element is formed of silicon or germanium, and has an aspherical surface as at least one surface thereof. The second lens element is formed of silicon or germanium, and has an aspherical surface as at least one surface thereof.

Moreover, the following conditional formulae are fulfilled.

$$0.1\ \mu m < \lambda 2 - \lambda 1 < 1\ \mu m \tag{1}$$

$$3\ \mu m < \lambda 1 < 5\ \mu m \tag{2}$$

$$3\ \mu m < \lambda 2 < 5\ \mu m \tag{3}$$

where $\lambda 1$ represents the shorter wavelength-side wavelength of the half-maximum width of the transmission wavelength range of the band-pass filter; and $\lambda 2$ represents the longer wavelength-side wavelength of the half-maximum width of the transmission wavelength range of the band-pass filter.

Although embodiments of the present invention have been described and illustrated in detail, it is clearly understood that the same is by way of illustration and example only and not limitation, the scope of the present invention should be interpreted by terms of the appended claims.

Arranging a first lens element and a second lens element in a negative-positive power arrangement as described above results in a so-called retrofocus construction, and this makes it possible to secure a long back focus as compared with the focal length. As a result, an aperture stop can be arranged between the second lens element and the image surface.

As will be easily understood from the Planck's law, the amount of infrared radiation in the wavelength band of 3 to 5 μm is far lower than that of visible light in the light radiated from the sun, and is far lower than that of so-called far-infrared radiation in the wavelength band of 8 to 14 μm in the light radiated from the environment such as the ground surface. It is thus difficult to perform imaging by use of a so-called uncooled sensor as is used in imaging in the visible and far-infrared regions; instead, very little light has to be sensed by use of a cooled sensor. Examples of such cooled sensors include so-called quantum sensors that use such sensing materials as indium antimonide (InSb), platinum silicide (PtSi), and mercury cadmium telluride (HgCdTe).

Since a cooled sensor senses very little radiation light, the light radiated from an aperture stop, a lens holding member, and the like cannot be ignored. As a solution, an aperture stop is arranged between the second lens element and the image surface, and the aperture stop is cooled to act as a cold aperture; it is thus possible to suppress the light radiated from the aperture stop and to shield the light radiated from the lens holding member.

For example, in a construction where an aperture stop is arranged between the first and second lens elements, axial and peripheral rays pass through different positions. This makes it possible to correct separately the aberrations that occur at the center and at the periphery with different sensitivities. Thus, it is relatively easy to correct aberrations. By contrast, in a construction where an aperture stop is arranged between the second lens element and the image surface, axial and peripheral rays pass through similar positions. This diminishes the above-mentioned effect, making correction of aberrations difficult. Giving the first lens element a meniscus shape convex to the object surface side and the second lens element a biconvex shape makes it possible, even with the aperture stop arranged between the second lens element and the image surface, to correct both spherical aberration and distortion.

In a construction where a band-pass filter is arranged between the second lens element and the image surface, it is possible to arrange the band-pass filter close to the cold aperture, and thus to cool the band-pass filter as well as the cold aperture in terms of mechanical construction. Cooling the band-pass filter provides the effect of minimizing the light radiated from the band-pass filter. Thus, the band-pass filter may be arranged on the image side of the cold aperture, or may be arranged on the object side of the cold aperture.

Using a high-refractive-index material such as silicon (Si) or germanium (Ge) helps reduce the angle of incidence and the angle of emergence with respect to a lens element, and this provides the effect of reducing the amounts of aberrations at the lens surfaces. If large amounts of aberrations occur at the lens surfaces, correcting those aberrations requires the arrangement of a large number of lens elements.

Arranging an aspherical surface as at least one surface of each of the first and second lens elements makes it possible, even with as few as two lens elements, to correct astigmatism, coma, and the like satisfactorily. Using as few as two lens elements helps reduce the number of times that light is incident on and emergent from lens surfaces and thus the number of times that light is reflected at lens surfaces. This provides the effect of minimizing the loss of light. It is thus possible to secure high transmittance through the imaging optical system.

The wavelength band of 3 to 5 μm includes the absorption wavelength bands of various hydrocarbon-based substances such as methane and propane. To enable the detection of such substances, conditional formulae (2) and (3) have to be fulfilled; to enable an accurate detection of gases as mentioned above, conditional formula (1) has to be fulfilled. Below the lower limit of conditional formula (1), the amount of light that passes through the imaging optical system to reach the sensor is so small that imaging takes a long time. As a result, camera shake, subject shake, and the like are more likely. On the other hand, above the upper limit of conditional formula (1), the amount of light incident on the sensor is so large as compared with the amount of light absorbed by hydrocarbon-based substances as mentioned above that the absorption by those substances is difficult to detect.

Generally, an optical system for the wavelength band of 3 to 5 μm is used over the entire span of the wavelength band of 3 to 5 μm. To secure a sufficient amount of light, a construction that fulfills conditional formulae (1) to (3) noted above is required to have an f-number faster than usual. For example, it is preferable that the f-number be faster than f/2.

With the distinctive construction described above, it is possible to build an infrared optical system, and an imaging optical device provided with it, that can be incorporated in a cooled sensor and that provides high transmittance and high optical performance with as few as two lens elements. By employing such an infrared optical system or an imaging optical device in digital appliances such as gas detection devices and camera systems (for example, surveillance cameras, security cameras, vehicle-mounted cameras, and aircraft cameras), it is possible to add a high-performance infrared image input function to those digital appliances at low cost, and to contribute to making the digital appliances low-cost, high-performance, versatile, and otherwise improving them. Conditions and the like preferable, in building an infrared optical system compatible with a cooled sensor with two lens elements while achieving high transmittance and high performance as described above, to obtain those effects with a good balance, and to achieve still higher optical performance, weight and size reduction, and the like will be described below.

It is preferable that conditional formula (1a) below be fulfilled.

$$0.2 \ \mu m < \lambda 2 - \lambda 1 < 0.6 \ \mu m \tag{1a}$$

Conditional formula (1a) defines, within the conditional range defined by conditional formula (1) noted above, a further preferable conditional range from the above-mentioned and other perspectives. Thus, by fulfilling, preferably, conditional formula (1a), it is possible to augment the above-mentioned effects.

It is preferable that conditional formula (4) below be fulfilled.

$$0.4 < (r3+r4)/(r3-r4) < 1 \tag{4}$$

where
r3 represents the radius of curvature of the object-side surface of the second lens element; and
r4 represents the radius of curvature of the image surface-side surface of the second lens element.

Conditional formula (4) defines the preferred shape factor of the second lens element which has a biconvex shape. Fulfilling conditional formula (4) makes it possible to correct spherical aberration and distortion with a good balance. Below the lower limit of conditional formula (4), the shape is such that the radii of curvature on the opposite sides are close together. Above the upper limit of conditional formula (4), the shape is such that the curvature on the object side is gentle while the curvature on the image surface side is sharp. In either case, it is difficult to correct spherical aberration and distortion with a good balance. In particular, above the upper limit of conditional formula (4), it is also difficult to correct spherical aberration and astigmatism with a good balance.

It is preferable that conditional formula (5) below be fulfilled.

$$-2.2 < f1/f2 < -1.6 \tag{5}$$

where
f1 represents the focal length of the first lens element; and
f2 represents the focal length of the second lens element.

Conditional formula (5) defines the preferred power ratio of the first lens element to the second lens element. Fulfilling conditional formula (5) makes it possible to correct spherical aberration, astigmatism, and distortion with a good balance. Above the upper limit of conditional formula (5), it is difficult to correct astigmatism and distortion with a good balance. Below the lower limit of conditional formula (5), it is difficult to correct astigmatism and spherical aberration with a good balance. Moreover, below the lower limit of conditional formula (5), the optical power of the first lens element is so low as compared with the optical power of the second lens element that keeping the focal length of the entire system results in an increased total length.

It is preferable that conditional formula (6) below be fulfilled.

$$3.3 < TT/f < 4.1 \tag{6}$$

where
TT represents the distance from the vertex of the object-side surface of the first lens element to the paraxial image point; and
f represents the focal length of the entire system.

Conditional formula (6) defines the preferred total length TT of the infrared optical system relative to the focal length f of the entire system. Fulfilling conditional formula (6) makes it possible to reduce ghost light while achieving weight and size reduction in the entire system. Above the upper limit of conditional formula (6), the first and second lens elements both tend to have increased effective radii, possibly leading to increased weight and increased cost. Below the lower limit of conditional formula (6), the lens interval is so small that interfacial reflection produces ghost light which tends to be incident on the sensor. In a case where a cooled sensor is used, even slight ghost light is highly likely to affect the imaging result; thus, it is preferable to secure a lens interval large enough to fulfill conditional formula (6).

It is preferable that conditional formula (7) below be fulfilled.

$$1<f2/f<1.4 \qquad (7)$$

where f2 represents the focal length of the second lens element; and f represents the focal length of the entire system.

Conditional formula (7) defines the preferred focal length f2 of the second lens element relative to the focal length f of the entire system. Fulfilling conditional formula (7) makes it possible to correct spherical aberration and astigmatism with a good balance. Below conditional formula (7), astigmatism is so large that it cannot be corrected with the first lens element alone. Above the upper limit of conditional formula (7), the optical power of the second lens element is so low that it is difficult to suppress spherical aberration and astigmatism satisfactorily while suppressing the total length. Moreover, an increased total length and an increased effective radius of the first lens element tend to result.

It is preferable that neither of the first and second lens elements have, as any surface thereof, a diffractive surface with surface relief or a Fresnel surface. In optical systems for use with so-called far-infrared radiation in the wavelength band of 8 to 14 μm, it is customary to correct chromatic aberration by use of a diffractive surface. However, diffracted light corresponding to high-order terms tends to become ghost light or flair components. Moreover, a diffractive surface, by its nature, inevitably has precipitous facets, and reflection and refraction at those precipitous facets produce ghost light and flair component like those just mentioned. Since a cooled sensor is highly sensitive, such unnecessary light may act as large noise and interfere with imaging. This applies not only to a diffractive surface with surface relief but also to a Fresnel surface.

An infrared optical system according to the present invention is suitable for use as an imaging optical system in digital appliances furnished with an infrared image input function (for example, gas leak detection systems equipped with infrared cameras). By combining it with a cooled sensor or the like for imaging, it is possible to build an infrared imaging optical device that optically takes in an infrared image of a subject to output an electrical signal representing it. An imaging optical device is an optical device that constitutes the principal component of a camera used to take still and moving images of a subject, and is composed of, for example, from the object side (that is, from the subject side), an infrared optical system that forms an infrared optical image of an object and an image sensor (corresponding to, for example, a cooled sensor) that converts the infrared optical image formed by the infrared optical system into an electrical signal. By arranging the infrared optical system with the distinctive construction described above such that the infrared optical image of the subject is formed on the light-receiving surface (that is, the imaging surface) of the image sensor, it is possible to build an imaging optical device, and a digital appliance provided with it, that is compact, low-cost, and high-performance.

Examples of digital appliances furnished with an infrared image input function include infrared cameras, surveillance cameras, security cameras, vehicle-mounted cameras, aircraft cameras, marine vessel cameras, fire detection cameras, and also include gas detection systems, gas leak detection systems, night-vision devices, thermographic devices, infrastructure monitoring systems (for monitoring high-tension cables, unusual heat sources in factories and plants, deterioration of structures, and the like).

As will be understood from the examples enumerated above, by use of an imaging optical device for infrared radiation, not only is it possible to build an infrared camera system, but it is also possible, by incorporating the imaging optical device in various appliances, to furnish them additionally with an infrared camera function, a high-vision function, a temperature measurement function, and the like. For example, by building a gas detection device equipped with an infrared camera which is furnished with, as an infrared image input function, a function of imaging contrast differences resulting from absorption of infrared radiation in absorption wavelength bands peculiar to hydrocarbon-based substances (methane, ethane, propane, butane, and the like), it is possible to detect, for example, a gas leak or the like that cannot be detected on the basis of visible light. By making the cooling structure compact, it is also possible to build a digital appliance furnished with an infrared image input function such as a smartphone equipped with an infrared camera.

Figure 15:
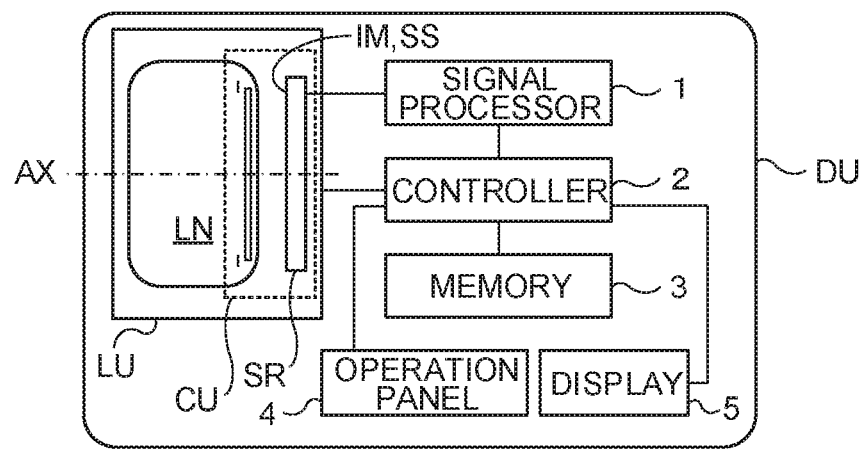
FIG. 15 is a schematic diagram showing an example of an outline of the configuration of a digital appliance incorporating an infrared optical system.

FIG. 15 shows, in a schematic sectional view, an example of an outline of the configuration of a digital appliance DU as one example of a digital appliance furnished with an infrared image input function. An imaging optical device LU incorporated in the digital appliance DU shown in FIG. 15 includes, from the object side (that is, from the subject side), an infrared optical system LN (AX representing the optical axis) which forms an infrared optical image (image surface) IM of an object and an image sensor (cooled sensor) SR which converts the optical image IM formed on the light-receiving surface (imaging surface) SS by the infrared optical system LN into an electrical signal. The infrared optical system LN is a single-focal-length lens system composed of two single lens elements, a cold aperture, and a band-pass filter, and is configured to form an optical image IM of infrared radiation on the light-receiving surface SS which constitutes the photoelectric converter of the image sensor SR.

Any plane-parallel plate other than the band-pass filter incorporated in the infrared optical system LN may be arranged. As such a plane-parallel plate, a window for sealing in a cooler CU may be arranged close to the cold aperture or, with consideration given to resistance to scratches, chemicals, and the like, a cover member or a window member that transmits infrared radiation in the wavelength band of 3 to 5 μm may be arranged outward of the first lens element located at the most object-side position. In a case where a digital appliance DU furnished with an image input function is built with the imaging optical device LU, the imaging optical device LU is usually arranged inside the body of the digital appliance DU; by contrast, a camera function can be implemented in any manner that suits the needs. For example, an imaging optical device LU built as a unit can be configured to be removable from, or rotatable relative to, the body of a digital appliance DU.

The digital appliance DU includes, in addition to the imaging optical device LU, a signal processor 1, a controller 2, a memory 3, an operation panel 4, a display 5, and the like. The signal generated by the image sensor SR is subjected to predetermined digital image processing, image compression, and the like in the signal processor 1, and is recorded, as a digital image signal, in the memory 3 (a semiconductor memory, an optical disc, or the like) or, as the case may be, is transferred to an external appliance via a cable or after being converted into an infrared signal or the like (for example, a communication function of a mobile telephone). The controller 2 comprises a microcomputer, and performs in a centralized manner the control of imaging functions (such as still and moving image shooting functions) and of functions such as image playback functions and the control of lens moving mechanisms for focusing and the like. For example, the controller 2 controls the imaging optical device LU to make it at least either take a still image or take a moving image of the subject. The display 5 includes a display such as a liquid crystal monitor, and displays images by use of an image signal resulting from conversion by the image sensor SR or image information recorded in the memory 3. The operation panel 4 includes operation members such as operation buttons (for example, a shutter-release button) and operation dials (for example, a shooting mode dial), and conveys the information entered by an operator to the controller 2.

FIGS. 1, 3, and 13 show an optical section of the infrared optical system LN according to a first to a seventh embodiment, respectively, in the infinity-focused condition. In all of the first to seventh embodiments, the infrared optical system LN is composed of, from the object side, a first lens element L1 which has a negative optical power and which has a meniscus shape convex to the object side and a second lens element L2 which has a positive optical power and which has a biconvex shape (all optical powers are given in paraxial values). In the first to third embodiments, the first and second lens elements L1 and L2 both have aspherical surfaces as both surfaces thereof. In the fourth, fifth, and seventh embodiments, the first and second lens elements L1 and L2 both have an aspherical surface as the object-side surface thereof. In the sixth embodiment, the first lens element L1 has aspherical surfaces as both surfaces thereof and the second lens element L2 has an aspherical surface as the object-side surface thereof.

In the first and sixth embodiments, the first lens element L1 is formed of germanium. In the second to fifth and seventh embodiments, the first lens element L1 is formed of silicon. In all of the first to seventh embodiments, the second lens element L2 is formed of silicon, the aperture stop (cold aperture) ST is arranged between the second lens element L2 and the image surface IM, and the band-pass filter BPF is arranged between the aperture stop ST and the image surface IM, close to the aperture stop ST. In all the embodiments described above, a window for sealing in the cooler CU (FIG. 15) may be arranged close to the aperture stop ST, and, with consideration given to resistance to scratches, chemicals, and the like, a cover member or a window member that transmits infrared radiation in the wavelength band of 3 to 5 μm may be arranged outward of the first lens element L1 located at the most object-side position.

EXAMPLES

Hereinafter, the construction and the like of infrared optical systems embodying the present invention will be described more specifically by referring to the construction data and the like of practical examples. Examples 1 to 7 (EX1 to EX7) presented below are numerical examples corresponding to the first to seventh embodiments, respectively, described above, and the lens arrangement diagrams (FIGS. 1, 3, . . . , 13) showing the first to seventh embodiments also show the lenses' sectional shapes, lens arrangement, and the like in the corresponding ones of Examples 1 to 7 respectively.

In the construction data of each practical example, listed as surface data are, from left rightward, surface number, paraxial radius of curvature R (mm), axial surface-to-surface distance d (mm), refractive index N3.3 at a wavelength of 3.3 and dispersion v at wavelengths of 3 to 5 μm. The dispersion v indicates the degree of a dispersive property, and is defined by v=(N4−1)/(N3−N5) (where N3 represents the refractive index at a wavelength of 3 μm, N4 represents the refractive index at a wavelength of 4 and N5 represents the refractive index at a wavelength of 5 μm). Table 1 lists the refractive indices N3, N4, and N5 and the dispersions v of germanium (Ge) and silicon (Si).

A surface of which the surface number is marked with an asterisk (*) is an aspherical surface, of which the surface shape is defined by formula (AS) below in a local rectangular coordinate system (x, y, z) that has as its origin the vertex of the surface. Listed as aspherical surface data are aspherical surface coefficients and the like. In the aspherical surface data of each practical example, the coefficient of any unlisted term equals zero, and for all the data, E-n stands for $\times 10^{-n}$.

$$z=(C \cdot h^2)/[1+\sqrt{\{1-(1+K) \cdot C^2 \cdot h^2\}}]+\Sigma(Ai \cdot h^i) \quad (AS)$$

where h represents the height perpendicular to the z axis (optical axis AX) ($h^2=x^2+y^2$);

z represents the amount of sag in the optical axis AX direction at the height h (relative to the vertex of the surface);

C represents the curvature at the vertex of the surface (the reciprocal of the paraxial radius of curvature R);

K represents the conic constant; and

Ai represents the aspherical surface coefficient of order i (Σ representing the sum for i=4 to ∞).

Table 2 lists, as miscellaneous data, focal length f (mm) of the entire system, f-number (Fno), whole angle of view 2ω (°), total lens length TT (mm), backfocus fB (mm), image height Y' (mm), focal length f1 (mm) of the first lens element L1, focal length f2 (mm) of the second lens element L2, radius of curvature r3 (mm) of the object-side surface of the second lens element L2, and radius of curvature r4 (mm) of the image surface-side surface of the second lens element L2. Table 3 lists the values (all as observed at a wavelength of 3.2 μm) corresponding to the conditional formulae in each practical example. In Table 2, the total lens length TT is the distance from the vertex of the object-side surface of the first lens element L1 to the paraxial point, and the back focus fB is the distance from the last lens surface to the paraxial image surface as expressed in terms of an air-equivalent length.

Figure 4A:
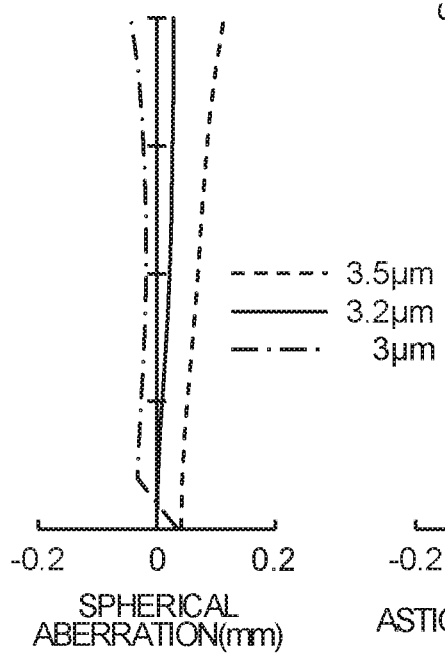
FIG. 4A to 4C are aberration diagrams of Example 2.
Figure 4B:
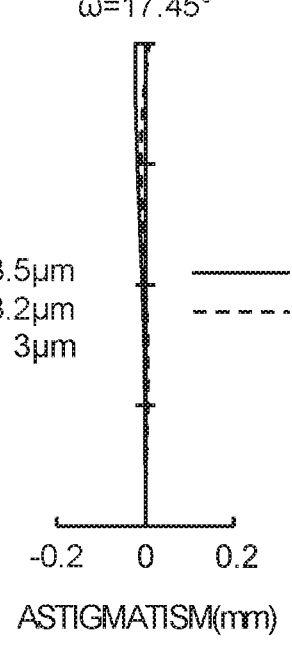
Figure 4C:
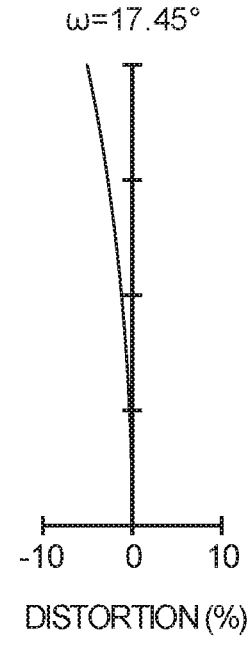
Figure 7:
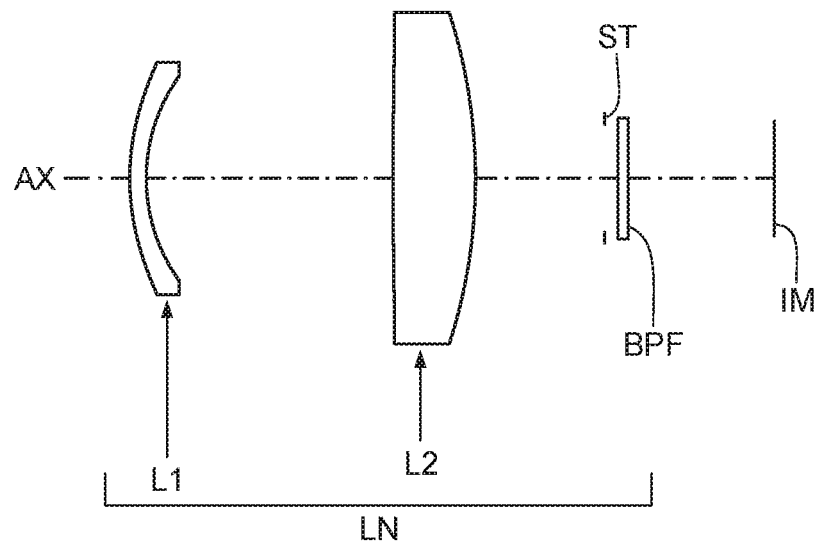
FIG. 7 is a lens arrangement diagram of a fourth embodiment (Example 4) of the present invention.
Figure 8A:
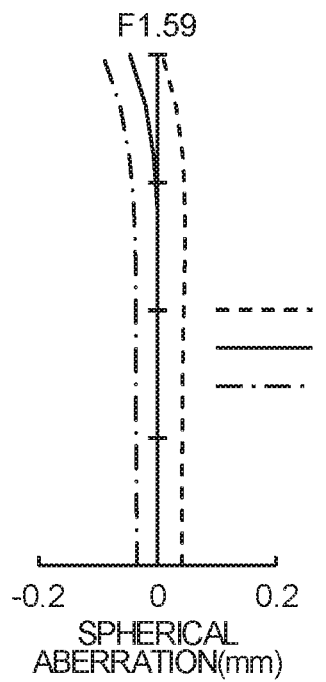
FIG. 8A to 8C are aberration diagrams of Example 4.
Figure 8B:
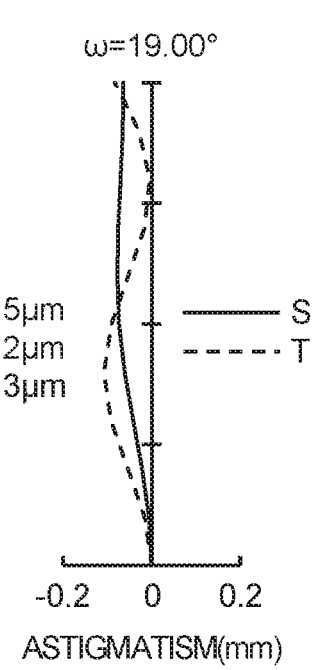
Figure 8C:
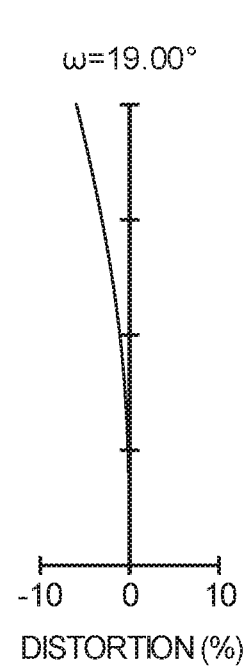
Figure 11:
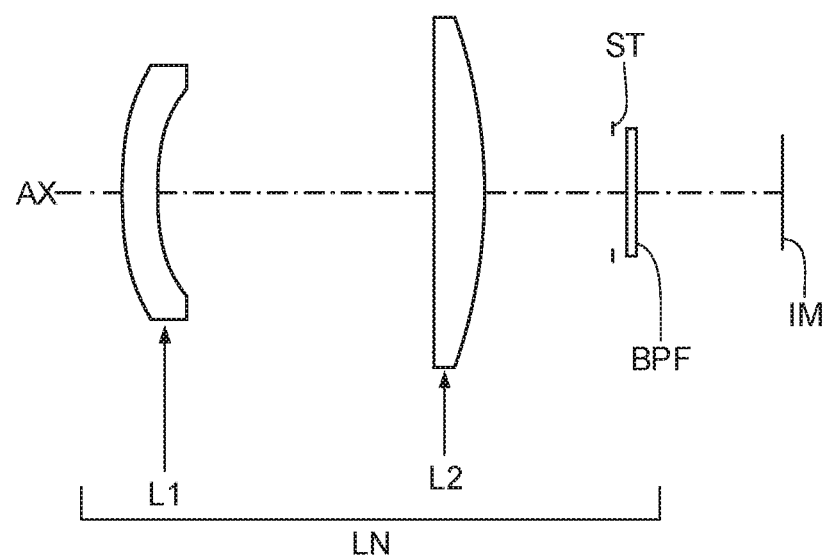
FIG. 11 is a lens arrangement diagram of a sixth embodiment (Example 6) of the present invention.
Figure 12A:
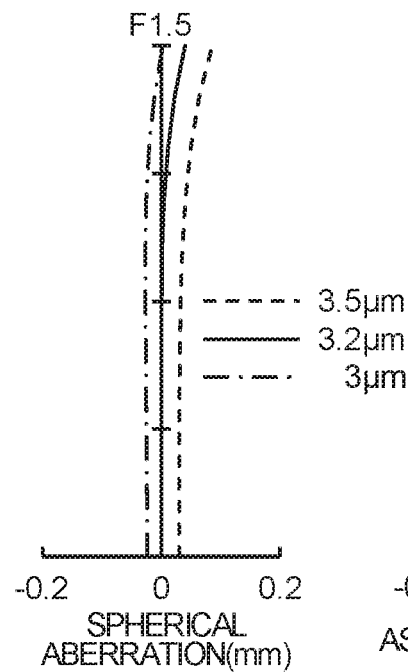
FIG. 12A to 12C are aberration diagrams of Example 6.
Figure 12B:
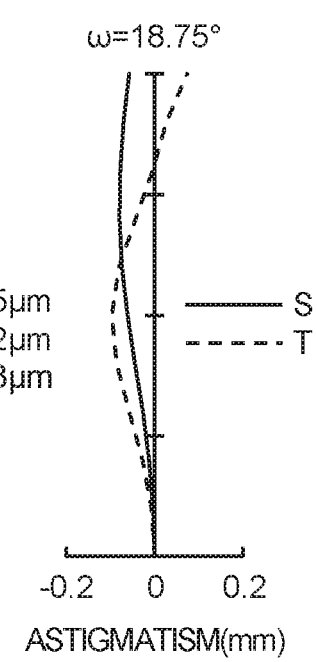
Figure 12C:

FIGS. 2A to 2C, 4A to 4C, . . . , and 14A to 14C are aberration diagrams corresponding to Examples 1 to 7 (EX1 to EX7) respectively, of which FIGS. 2A, 4A, . . . , and 14A are spherical aberrations diagrams, FIGS. 2B, 4B, . . . , and 14B are astigmatism diagrams, and FIGS. 2C, 4C, . . . , and 14C are distortion diagrams. In the spherical aberrations diagrams, a solid line represents the amount of spherical aberration at the design wavelength (evaluation wavelength) of 3.2 mm, a dash-and-dot line represents the amount of spherical aberration at a wavelength of 3 μm, and a broken line represents the amount of spherical aberration at a wavelength of 3.5 μm, all as expressed in terms of the amount of displacement (mm) in the optical axis AX direction from the paraxial image surface, the vertical axis representing the f-number. In the astigmatism diagrams, a broken line T represents the tangential image surface at the design wavelength of 3.2 μm, and a solid line S represents the sagittal image surface at the design wavelength of 3.2 μm, both as expressed in terms of the displacement (mm) in the optical axis AX direction from the paraxial image surface, the vertical axis representing the half angle of view ω (°). In the distortion diagrams, the horizontal axis represents the distortion (%) at the design wavelength of 3.2 μm, and the vertical axis represents the half angle of view ω (°).

Example 1

Unit: mm

Surface Data

| Surface No. | R | d | N3.3 | ν | Effective Radius |
|---|---|---|---|---|---|
| 1(Object Surface) | ∞ | ∞ | | | |
| 2* | 21.045 | 1.500 | 4.036 | 103 | 14.94 |
| 3* | 17.216 | 35.766 | | | 14.02 |
| 4* | 211.880 | 7.334 | 3.433 | 234 | 28.69 |
| 5* | −82.061 | 13.400 | | | 28.82 |
| 6(Aperture Stop) | ∞ | 1.700 | | | 12.71 |
| 7 | ∞ | 1.200 | 4.036 | 103 | 12.19 |
| 8 | ∞ | 20.003 | | | 12.11 |
| 9(Image Surface) | ∞ | | | | 6.02 |

Aspherical Surface Data

| Surface No. | K | A4 | A6 | A8 | A10 |
|---|---|---|---|---|---|
| 2 | −0.73 | 5.489E−06 | −1.405E−07 | 1.723E−10 | −9.856E−14 |
| 3 | −0.84 | 1.794E−05 | −1.861E−07 | 2.456E−10 | −7.595E−14 |
| 4 | −13.24 | −1.962E−06 | 4.779E−10 | 2.667E−15 | 2.404E−17 |
| 5 | 1.35 | −3.162E−07 | 3.180E−10 | −1.274E−13 | 1.148E−16 |

Example 2

Unit: mm

Surface Data

| Surface No. | R | d | N3.3 | ν | Effective Radius |
|---|---|---|---|---|---|
| 1(Object Surface) | ∞ | ∞ | | | |
| 2* | 24.716 | 1.500 | 3.433 | 234 | 15.0 |
| 3* | 19.283 | 35.907 | | | 14.1 |
| 4* | 205.267 | 7.193 | 3.433 | 234 | 28.4 |
| 5* | −83.662 | 13.400 | | | 29.0 |
| 6(Aperture Stop) | ∞ | 1.700 | | | 12.7 |
| 7 | ∞ | 1.200 | 4.036 | 103 | 12.2 |
| 8 | ∞ | 20.003 | | | 12.1 |
| 9(Image Surface) | ∞ | | | | 6.0 |

Aspherical Surface Data

| Surface No. | K | A4 | A6 | A8 | A10 |
|---|---|---|---|---|---|
| 2 | −0.16 | 8.376E−06 | −1.464E−07 | 1.841E−10 | −2.255E−13 |
| 3 | −0.56 | 2.278E−05 | −1.713E−07 | 1.880E−10 | −2.121E−13 |
| 4 | −6.75 | −1.916E−06 | 5.254E−10 | 6.361E−14 | 3.523E−17 |
| 5 | 1.26 | −2.744E−07 | 3.519E−10 | −9.287E−14 | 1.517E−16 |

Example 3

Unit: mm

Surface Data

| Surface No. | R | d | N3.3 | ν | Effective Radius |
|---|---|---|---|---|---|
| 1(Object Surface) | ∞ | ∞ | | | |
| 2* | 31.255 | 2.000 | 3.433 | 234 | 14.8 |
| 3* | 22.927 | 32.883 | | | 13.9 |
| 4* | 526.573 | 9.717 | 3.433 | 234 | 29.1 |
| 5* | −65.765 | 13.400 | | | 29.0 |

-continued

| | | Unit: mm | | | |
|---|---|---|---|---|---|
| 6(Aperture Stop) | ∞ | 1.700 | | | 12.6 |
| 7 | ∞ | 1.200 | 4.036 | 103 | 12.1 |
| 8 | ∞ | 20.003 | | | 12.0 |
| 9(Image Surface) | ∞ | | | | 6.0 |

| Aspherical Surface Data | | | | | |
|---|---|---|---|---|---|
| Surface No. | K | A4 | A6 | A8 | A10 |
| 2 | 0.41 | 5.430E−05 | −2.214E−07 | 1.028E−10 | −4.660E−13 |
| 3 | 0.94 | 6.596E−05 | −2.080E−07 | −6.881E−10 | −2.058E−13 |
| 4 | 15.00 | −1.789E−06 | 1.182E−09 | 8.026E−14 | 1.456E−16 |
| 5 | 0.50 | 2.598E−07 | 5.654E−10 | 3.885E−14 | 3.795E−16 |

Example 4

| | | Unit: mm | | | |
|---|---|---|---|---|---|

| | | Surface Data | | | |
|---|---|---|---|---|---|
| Surface No. | R | d | N3.3 | ν | Effective Radius |
| 1(Object Surface) | ∞ | ∞ | | | |
| 2* | 28.803 | 2.000 | 3.433 | 234 | 12.9 |
| 3 | 21.015 | 29.875 | | | 11.8 |
| 4* | 476.693 | 10.000 | 3.433 | 234 | 18.2 |
| 5 | −64.238 | 15.600 | | | 19.0 |
| 6(Aperture Stop) | ∞ | 1.700 | | | 6.5 |
| 7 | ∞ | 1.200 | 4.036 | 103 | 6.5 |
| 8 | ∞ | 17.700 | | | 6.5 |
| 9(Image Surface) | ∞ | | | | 6.5 |

| Aspherical Surface Data | | | | | |
|---|---|---|---|---|---|
| Surface No. | K | A4 | A6 | A8 | A10 |
| 2 | 2.12 | −1.473E−05 | −7.280E−08 | 1.991E−10 | −1.263E−12 |
| 4 | 15.00 | −2.146E−06 | 2.152E−09 | −3.450E−12 | 2.527E−15 |

Example 5

| | | Unit: mm | | | |
|---|---|---|---|---|---|

| | | Surface Data | | | |
|---|---|---|---|---|---|
| Surface No. | R | d | N3.3 | ν | Effective Radius |
| 1(Object Surface) | ∞ | ∞ | | | |
| 2* | 20.765 | 2.000 | 3.433 | 234 | 13.6 |
| 3 | 16.119 | 33.118 | | | 12.0 |
| 4* | 1155.698 | 8.782 | 3.433 | 234 | 19.3 |
| 5 | −61.284 | 15.500 | | | 20.0 |
| 6(Aperture Stop) | ∞ | 1.700 | | | 6.9 |
| 7 | ∞ | 1.200 | 4.036 | 103 | 6.9 |
| 8 | ∞ | 17.700 | | | 6.9 |
| 9(Image Surface) | ∞ | | | | 6.6 |

| Aspherical Surface Data | | | | | |
|---|---|---|---|---|---|
| Surface No. | K | A4 | A6 | A8 | A10 |
| 2 | 0.41 | −6.641E−06 | −5.645E−08 | 1.651E−10 | −8.177E−13 |
| 4 | −15.00 | −2.381E−06 | 3.466E−09 | −6.439E−12 | 5.655E−15 |

Example 6

| | Unit: mm | | | | |
|---|---|---|---|---|---|
| Surface Data | | | | | |
| Surface No. | R | d | N3.3 | ν | Effective Radius |
| 1(Object Surface) | ∞ | ∞ | | | |
| 2* | 67.749 | 4.284 | 4.036 | 103 | 14.2 |
| 3* | 42.528 | 33.447 | | | 12.0 |
| 4* | 794.643 | 6.169 | 3.433 | 234 | 19.5 |
| 5 | −63.073 | 15.500 | | | 20.0 |
| 6(Aperture Stop) | ∞ | 1.700 | | | 7.0 |
| 7 | ∞ | 1.200 | 4.036 | 103 | 6.9 |
| 8 | ∞ | 17.700 | | | 6.9 |
| 9(Image Surface) | ∞ | | | | 6.5 |
| Aspherical Surface Data | | | | | |
| Surface No. | K | A4 | A6 | A8 | A10 |
| 2 | 3.11 | 4.173E−05 | −2.980E−08 | −1.014E−11 | −3.342E−13 |
| 3 | 1.13 | 6.048E−05 | 6.557E−08 | 3.757E−10 | −3.955E−12 |
| 4 | 15.00 | −1.856E−06 | 9.206E−10 | −1.300E−12 | 1.232E−15 |

Example 7

| | Unit: mm | | | | |
|---|---|---|---|---|---|
| Surface Data | | | | | |
| Surface No. | R | d | N3.3 | ν | Effective Radius |
| 1(Object Surface) | ∞ | ∞ | | | |
| 2* | 24.895 | 3.000 | 3.433 | 234 | 14.3 |
| 3 | 19.079 | 30.849 | | | 12.5 |
| 4* | 784.783 | 10.000 | 3.433 | 234 | 18.1 |
| 5 | −64.655 | 15.551 | | | 19.0 |
| 6 | ∞ | 1.700 | | | 6.5 |
| 7 | ∞ | 1.200 | 4.036 | 103 | 6.5 |
| 8 | ∞ | 17.700 | | | 6.5 |
| 9(Image Surface) | ∞ | | | | 6.5 |
| Aspherical Surface Data | | | | | |
| Surface No. | K | A4 | A6 | A8 | A10 |
| 2 | 0.82 | −8.292E−06 | −4.275E−08 | 9.596E−11 | −5.000E−13 |
| 4 | −1.55 | −1.994E−06 | 3.057E−09 | −5.539E−12 | 4.498E−15 |

TABLE 1

| | N5 | N4 | N3 | ν | |
|---|---|---|---|---|---|
| Si | 3.4256 | 3.4289 | 3.4360 | 234 | 50 |
| Ge | 4.0153 | 4.0242 | 4.0446 | 103 | |

TABLE 2

| Miscellaneous Data | | | | | | | |
|---|---|---|---|---|---|---|---|
| | Example 1 | Example 2 | Example 3 | Example 4 | Example 5 | Example 6 | Example 7 |
| f | 20.1 | 20.1 | 20 | 20 | 20 | 20 | 22.9 |
| Fno | 1 | 1 | 1 | 1.59 | 1.5 | 1.5 | 1.59 |
| 2ω | 34.9 | 34.9 | 34.7 | 38.0 | 37.5 | 37.5 | 33.0 |
| TT | 80.90 | 80.90 | 80.90 | 78.08 | 80.00 | 80.00 | 80.00 |
| fB | 35.40 | 35.40 | 35.40 | 35.30 | 35.20 | 35.20 | 35.25 |
| Y' | 6.0 | 6.0 | 6.0 | 6.5 | 6.5 | 6.5 | 6.5 |
| f1 | −44.18 | −44.82 | −42.62 | −39.05 | −42.61 | −43.14 | −52.90 |

TABLE 2-continued

Miscellaneous Data

| | Example 1 | Example 2 | Example 3 | Example 4 | Example 5 | Example 6 | Example 7 |
|---|---|---|---|---|---|---|---|
| f2 | 24.75 | 24.87 | 24.31 | 23.58 | 24.04 | 24.14 | 24.76 |
| r3 | 211.88 | 205.27 | 526.57 | 476.69 | 1155.70 | 794.64 | 784.78 |
| r4 | −82.06 | −83.66 | −65.77 | −64.24 | −61.28 | −63.07 | −64.65 |

TABLE 3

| Conditional Formula | Example 1 | Example 2 | Example 3 | Example 4 | Example 5 | Example 6 | Example 7 |
|---|---|---|---|---|---|---|---|
| (1) $\lambda 2 - \lambda 1$ (μm) | 0.2 | 0.2 | 0.2 | 0.2 | 0.2 | 0.2 | 0.2 |
| (2) $\lambda 1$ (μm) | 3.2 | 3.2 | 3.2 | 3.2 | 3.2 | 3.2 | 3.2 |
| (3) $\lambda 2$ (μm) | 3.4 | 3.4 | 3.4 | 3.4 | 3.4 | 3.4 | 3.4 |
| (4) (r3 + r4)/(r3 − r4) | 0.44 | 0.42 | 0.78 | 0.76 | 0.90 | 0.85 | 0.85 |
| (5) f1/f2 | −1.79 | −1.80 | −1.75 | −1.66 | −1.77 | −1.79 | −2.14 |
| (6) TT/f | 4.03 | 4.03 | 4.05 | 3.90 | 4.00 | 4.00 | 3.49 |
| (7) f2/f | 1.23 | 1.24 | 1.22 | 1.18 | 1.20 | 1.21 | 1.08 |

LIST OF REFERENCE SIGNS

DU digital appliance
LU imaging optical device
CU cooler
LN infrared optical system
L1 first lens element
L2 second lens element
ST aperture stop (cold aperture)
BPF band-pass filter
SR image sensor (cooled sensor)
SS light-receiving surface (imaging surface)
IM image surface (optical image)
AX optical axis
1 signal processor
2 controller
3 memory
4 operation panel
5 display

The invention claimed is:

1. An infrared optical system for use for imaging in a wavelength band of 3 to 5 μm, comprising, from an object side:
a first lens element having a negative optical power, the first lens element having a meniscus shape convex to the object side;
a second lens element having a biconvex shape; and
a cold aperture,
with a band-pass filter arranged between the second lens element and an image surface,
wherein
the first lens element is formed of silicon or germanium, the first lens element having an aspherical surface as at least one surface thereof,
the second lens element is formed of silicon or germanium, the second lens element having an aspherical surface as at least one surface thereof, and
conditional formulae (1) to (3) below are fulfilled:

$$0.1 \ \mu m < \lambda 2 - \lambda 1 < 1 \ \mu m \quad (1)$$

$$3 \ \mu m < \lambda 1 < 5 \ \mu m \quad (2)$$

$$3 \ \mu m < \lambda 2 < 5 \ \mu m \quad (3)$$

where
λ1 represents a shorter wavelength-side wavelength of a half-maximum width of a transmission wavelength range of the band-pass filter; and
λ2 represents a longer wavelength-side wavelength of the half-maximum width of the transmission wavelength range of the band-pass filter.

2. The infrared optical system according to claim 1, wherein
conditional formula (4) below is fulfilled:

$$0.4 < (r3+r4)/(r3-r4) < 1 \quad (4)$$

where
r3 represents a radius of curvature of an object-side surface of the second lens element; and
r4 represents a radius of curvature of an image surface-side surface of the second lens element.

3. The infrared optical system according to claim 1, wherein
conditional formula (5) below is fulfilled:

$$-2.2 < f1/f2 < -1.6 \quad (5)$$

where
f1 represents a focal length of the first lens element; and
f2 represents a focal length of the second lens element.

4. The infrared optical system according to claim 1, wherein
conditional formula (6) below is fulfilled:

$$3.3 < TT/f < 4.1 \quad (6)$$

where
TT represents a distance from a vertex of an object-side surface of the first lens element to a paraxial image point; and
f represents a focal length of the entire system.

5. The infrared optical system according to claim 1, wherein
conditional formula (7) below is fulfilled:

$$1 < f2/f < 1.4 \quad (7)$$

where
f2 represents a focal length of the second lens element; and
f represents a focal length of the entire system.

6. The infrared optical system according to claim 1, wherein
neither the first lens element nor the second lens element has, as any surface thereof, a diffractive surface with surface relief or a Fresnel surface.

7. An imaging optical device comprising:
an infrared optical system according to claim 1; and
an image sensor for converting an infrared optical image formed on an imaging surface into an electrical signal, wherein
the infrared optical system is arranged such that the infrared optical image of a subject is formed on the imaging surface of the image sensor.

8. A digital appliance comprising the imaging optical device according to claim 7 so as to be additionally furnished with at least one of a function of taking a still image of the subject or a function of taking a moving image of the subject.

9. An infrared camera system comprising the infrared optical system according to claim 1.

* * * * *